(12) United States Patent
Visentin et al.

(10) Patent No.: US 11,079,375 B2
(45) Date of Patent: Aug. 3, 2021

(54) METHOD FOR DETERMINING ACTIVE CONCENTRATIONS AND/OR KINETIC INTERACTION CONSTANTS IN COMPLEX BIOLOGICAL SAMPLES BY MEANS OF SURFACE PLASMON RESONANCE

(71) Applicants: UNIVERSITE DE BORDEAUX, Bordeaux (FR); CENTRE HOSPITALIER UNIVERSITAIRE DE BORDEAUX, Talence (FR); CENTRE NATIONAL DE LA RECHERCHE SCIENTIFIQUE, Paris (FR); INSERM (INSTITUT NATIONAL DE LA SANTE ET DE LA RECHERCHE MEDICALE), Paris (FR)

(72) Inventors: Jonathan Visentin, Bordeaux (FR); Carmelo Di Primo, Merignac (FR); Jean-Luc Taupin, Paris (FR)

(73) Assignees: UNIVERSITÉ DE BORDEAUX, Bordeaux (FR); CENTRE HOSPITALIER UNIVERSITAIRE DE BORDEAUX, Talence (FR); CENTRE NATIONAL DE LA RECHERCHE SCIENTIFIQUE, Paris (FR); INSERM (INSTITUT NATIONAL DE LA SANTÉ ET DE LA RECHERCHE MÉDICALE), Paris (FR)

( * ) Notice: Subject to any disclaimer, the term of this patent is extended or adjusted under 35 U.S.C. 154(b) by 197 days.

(21) Appl. No.: 16/083,529

(22) PCT Filed: Mar. 28, 2017

(86) PCT No.: PCT/FR2017/050702
§ 371 (c)(1),
(2) Date: Sep. 10, 2018

(87) PCT Pub. No.: WO2017/168083
PCT Pub. Date: Oct. 5, 2017

(65) Prior Publication Data
US 2020/0033264 A1 Jan. 30, 2020

(30) Foreign Application Priority Data
Mar. 29, 2016 (FR) ...................................... 1652699

(51) Int. Cl.
| | | |
|---|---|---|
| *G01N 33/553* | (2006.01) |
| *G01N 33/543* | (2006.01) |
| *G01N 21/552* | (2014.01) |
| *G01N 33/564* | (2006.01) |
| *G01N 33/569* | (2006.01) |
| *G01N 33/68* | (2006.01) |

(52) U.S. Cl.
CPC ..... *G01N 33/54373* (2013.01); *G01N 21/553* (2013.01); *G01N 33/543* (2013.01);
(Continued)

(58) Field of Classification Search
CPC .. G01N 21/553; G01N 33/543; G01N 33/564; G01N 33/56977; G01N 33/6854;
(Continued)

(56) References Cited

U.S. PATENT DOCUMENTS

2003/0059954 A1 3/2003 Vikholm et al.

OTHER PUBLICATIONS

Jiří Homola, Hana Vaisocherová, Jakub Dostálek, Marek Piliarik ("Multi-analyte surface plasmon resonance biosensing", Methods, 37, 2005, 26-36) (Year: 2005).*
(Continued)

*Primary Examiner* — Christopher L Chin
(74) *Attorney, Agent, or Firm* — Saliwanchik, Lloyd & Eisenschenk

(57) ABSTRACT

The invention relates to a method for determining active concentrations of an analyte and optionally kinetic constants
(Continued)

for the interaction of the analyte with a ligand in complex biological samples by means of surface plasmon resonance comprising the use of an auto-blank.

11 Claims, 4 Drawing Sheets

(52) U.S. Cl.
CPC ..... *G01N 33/564* (2013.01); *G01N 33/56977* (2013.01); *G01N 33/6854* (2013.01)

(58) Field of Classification Search
CPC ........... G01N 21/554; G01N 33/54373; G01N 33/553
USPC .................... 435/501, 288.7, 808; 422/82.11; 436/525, 805, 164, 811; 356/318
See application file for complete search history.

(56) References Cited

OTHER PUBLICATIONS

Shah et al "Calibration-free concentration analysis of protein biomarkers in human serum using surface plasmon resonance", Talanta, 2015, 144, 801-808 (Year: 2015).*

Ewa Pol "The Importance of Correct Protein Concentration for Kinetics and Affinity Determination in Structure-function Analysis", Journal of Visualized Experiments, 2010, 37, 1-7 (Year: 2010).*

Schlaf etal "Novel solid phase-based ELISA assays contribute to an improved detection of anti-HLA antibodies and to an increased reliability of pre- and post-transplant crossmatching", NDT Plus, 2010, 3(6), 527-538 (Year: 2010).*

GE Healthcare "Biacore™ concentration and ligand-binding analyses in late-stage development and quality control of biotherapeutics", GE Healthcare, 2015, 29148054 AA, 1-12 (Year: 2015).*

Schnaidt et al "HLA Antibody Specification using single-antigen beads—A technical solution for the prozone effect", Transplantation, 2011, 92: 510-515 (Year: 2011).*

Luo, R. "Guide SPR Data Processing on the ProteOn™ XPR36 Protein Interaction Array System" 2013, retrieved from the internet: URL:http://www.bio-rad.com/webroot/web/pdf/lsr/literature/Bulletin_6300.pdf, retrieved on Nov. 4, 2016, pp. 1-8.

Visentin, J. et al. "Calibration free concentration analysis by surface plasmon resonance in a capture mode" *Talanta*, 2016, pp. 478-485, vol. 148, No. 10.

Written Opinion in International Application No. PCT/FR2017/050702, dated May 31, 2017, pp. 1-8.

* cited by examiner

METHOD FOR DETERMINING ACTIVE CONCENTRATIONS AND/OR KINETIC INTERACTION CONSTANTS IN COMPLEX BIOLOGICAL SAMPLES BY MEANS OF SURFACE PLASMON RESONANCE

CROSS-REFERENCE TO RELATED APPLICATION

This application is the U.S. national stage application of International Patent Application No. PCT/FR2017/050702, filed Mar. 28, 2017.

FIELD OF THE INVENTION

The present invention relates to a process for determining active concentrations, and optionally kinetic interaction constants, of an analyte in complex biological samples by surface plasmon resonance (SPR).

TECHNOLOGICAL BACKGROUND OF THE INVENTION

During the first three decades of organ transplants, efforts have been concentrated on developing immunosuppressive treatments that act on T lymphocytes, with the main success story being calcineurin inhibitors which have made it possible to reduce the incidence of acute cellular rejection and increase the short-term survival of the transplanted organs. Nonetheless, the long-term survival of grafts has only been slightly improved. The development of techniques making it possible to detect anti-HLA antibodies has been illuminating in terms of these later graft losses, which appear to be predominantly due to the humoral alloimmune response. Indeed, regardless of the organ, the presence of donor-specific anti-HLA antibodies (DSA: donor-specific antibodies) gives rise to a procession of acute and/or chronic inflammatory lesions that affect the function and the survival of the graft on a more or less long-term scale. DSAs, of IgG isotype in particular, are a major cause of graft loss in organ transplants.

Anti-HLA DSAs recognize the HLA molecules of the donor, which are different to those of the recipient in terms of amino acid sequences. Indeed, since HLA molecules are highly polymorphic, the majority of organ transplants are carried out with differences between donors and recipients. These differences are distributed across different locations in the HLA molecule, in a localized manner, with a large proportion of the molecule being conserved from one antigen to another.

The Luminex® "single antigen" assays (SAFB) are currently the most precise and sensitive tools for identifying IgG anti-HLA DSAs in recipients' serum. SAFB measures a mean fluorescence intensity (MFI), used as a semi-quantitative value of the "strength" of the antibody. Beyond the biological positivity threshold, which may be defined from the mean background noise observed with the technique, the clinical positivity threshold has not yet been very well defined. The absence of reference material and the disparity in terms of MFI values obtained in the different histocompatibility laboratories and as a function of the supplier do not facilitate this task. Thus, MFI is not perfectly associated with clinical outcome, which may be due to several reasons. Firstly, class I SAFBs frequently detect denatured class I anti-HLA antibodies, which are incapable of binding to the cell surface and therefore have no clinical significance. Consequently, the detection of these denatured class I anti-HLA antibodies has a negative impact on the access to transplant, by erroneous over-estimation of the patient's immunization. Secondly, IgG anti-HLAs with a high MFI are capable of activating the complement at the surface of the beads, leading to an accumulation of C4 and C3 degradation products capable of reducing the detection of the IgG anti-HLAs by steric hindrance. It has also been demonstrated that IgM anti-HLAs were also capable of interfering with the detection of IgGs through competition for the epitope, steric hindrance and complement activation. Finally, since SAFB is an end-point technique, it does not reflect the manner in which the DSAs are interacting with the graft in vivo and does not make it possible to assess the kinetic constants of interaction between the DSAs and their targets, although these properties could have an influence on their pathogenicity.

SPR, on the other hand, is a technique which makes it possible to determine the kinetic interaction constants. SPR is based on changes in the reflective properties of a thin layer of gold, on which, on one side, a polarized light is directed through a prism before being reflected towards a photodetector and, on the other side, a ligand is immobilized and immersed in a flow of buffer. Under conditions of total internal reflection, the polarized light generates an evanescent wave that penetrates the thin layer of gold and over a few hundred nanometers into the buffer, where a portion of the photons will be absorbed. The photodetector measures the intensity of the reflected light, which makes it possible to observe, at a given angle, a minimum intensity corresponding to the absorption of the energy of the evanescent wave by the free surface electrons. The angle at which this minimum is found is referred to as the resonance angle and varies as a function of the mass present in the field of the evanescent wave close to the layer of gold, any change in mass therefore altering the refractive index. Therefore, SPR is a technique which does not require prior labeling of the studied molecules (it is "label-free").

In practice, the majority of SPR instruments use microarrays having an analysis surface separated into several lanes or spots. Once the ligand is attached to the surface, a solution containing the analyte to be studied is injected at a constant flow rate and for a given duration. The apparatus constantly measures, in "real time", the variation in the resonance angle due to the variation in mass at the surface of the lane. The signal measured as a function of time constitutes a sensorgram, the unit of which is the resonance unit (or RU). One RU corresponds to the binding of one ng of protein per mm². In the absence of injection of solution to be tested, a running buffer flows over the surface and the signal does not vary as a function of time. During the injection of an analyte that is capable of binding to the immobilized ligand, the mass increases at the surface of the track. The resonance angle varies since the refractive index changes. The signal measured (RU) increases as a function of time. Thus, it is possible to study, in real time, the interaction of an analyte with a given ligand. It should be noted that the variation of the resonance angle during the formation of the complex depends on the weight ratio between the analyte and the ligand. Moreover, before being able to interact with the ligand which is immobilized in the polymer matrix, the analyte must diffuse from the flow (or bulk), passing above this matrix towards this matrix according to a constant $k_m$, which is the mass transport coefficient.

The $k_m$ depends on the coefficient of diffusion of the analyte (D), on the injection flow rate (f) and on the dimensions of the measuring cell. The coefficient of diffusion of the analyte depends on the molecular weight thereof, the coefficient of friction thereof and also the relative viscosity of the solution used.

At the end of the injection, the running buffer takes over, the analyte dissociates and is carried into the flow of buffer. Since the mass is decreasing at the surface of the lane, the resonance angle varies in the other direction. The signal (RU) therefore decreases with time. This dissociation phase is more or less rapid depending on the rate of dissociation of the complex, independent of the flow rate of buffer.

For the majority of antigen-antibody pairs (Ag-Ab), the rate of dissociation of the complex is very slow. This requires the injection of a regeneration solution over the surface in order to instantly dissociate the complex in order to be able to carry out another cycle of analyte injection. The regeneration solution is often formed of an acidic or basic solution having a significant ionic strength or containing detergents and organic compounds. This solution must totally and instantly dissociate the analyte-ligand complexes without degrading the immobilized ligand or the surface of the microarray. This makes it possible to multiply the injections over the surface without having to change the lane or re-immobilize an identical amount of ligand.

Within the context of the analysis of HLA antibodies, direct (covalent) immobilization of the HLA molecule on the microarray cannot be envisaged because the HLA molecule does not withstand regeneration. A capture system has therefore been developed and tested, to make it possible to overcome this difficulty (Visentin et al., 2016, Talanta, 148, 478-485). Thus, an anti-β2-microglobulin antibody (invariable chain associated with all HLA class I molecules) is immobilized covalently on the surface and serves to capture HLA molecules, representing the ligand, which may then be the site of interaction with anti-HLA antibodies, the analyte.

SPR makes it possible to determine the active concentration of an analyte, that is to say the concentration of the fraction of analyte capable of interacting with the ligand. Unlike other methods, this measurement can be carried out without a calibration curve. The method, known under the name of calibration-free concentration analysis or CFCA, is based on the phenomenon of mass transport limitation described above. If the rate of diffusion of the analyte towards the surface is slower than the rate of association with its ligand, the apparent rate of association will be decreased because it will depend on the diffusion of the analyte towards its target. For an analyte used under the same conditions of concentration, temperature and solution, the coefficient of mass transport ($k_m$) will then only depend on the flow rate. An initial association slope will then be observed, which is different depending on the flow.

It has thus been shown that SPR used in capture mode (Visentin et al., 2016, Talanta, 148, 478-485) made it possible to determine the active concentration and the kinetic interaction constants of monoclonal anti-HLA (Human Leukocyte Antigens) antibodies in a simple medium (physiological buffer). To date, this is the only method capable of doing so.

The use of CFCA is highly important in the context of anti-HLA antibodies originating from patients, given that it is by definition impossible to produce a calibration curve. Since each individual a priori has unique antibodies in terms of affinity with their HLA target, there is no reference material.

The use of a slow flow, of a large amount of immobilized ligand and of a weak concentration of analyte promotes limitation by mass transport. In the context of this application in capture mode, this requires immobilizing a very large amount of capture antibodies on the surface. The analyte is then injected according to two different flow rates, one slow and one fast. The comparison of the rates of association as a function of the flow rate used makes it possible to calculate the active concentration of the analyte.

SPR also makes it possible to determine the affinity of the analyte-ligand complex by injecting increasing concentrations of analyte over the surface. The experiments may be carried out in several cycles of association-dissociation then regeneration [multiple cycle kinetics analysis (MCK)] or by injecting increasing concentrations of the analyte until the target reaches saturation, without a regeneration cycle between the injections [single cycle kinetics analysis (SCK)]. These two methods have already been used in capture mode.

The analysis software makes it possible to perform an adjustment or "fit" of the sensorgrams according to a given interaction model, most commonly a simple 1:1 bimolecular model. The elementary association and dissociation constants, $k_a$ and $k_d$ respectively, are determined directly from this analysis.

It is important to note that determining these parameters requires precise knowledge of the active concentration of the analyte, that is to say the concentration of the fraction of the sample that is actually capable of interacting with the ligand. Indeed, the knowledge of the concentration of the injected analyte is necessary in order to analyze the kinetic data. In the context of the study of Ag-Ab pairs, determining the concentration of the antibody by spectrophotometric or colorimetric techniques is crude since these techniques can only measure a total concentration. They do not dispense with the impurities which result from the purification and which will contribute to the measured value. They also do not make it possible to estimate the fraction of denatured antibodies during the purification.

Unfortunately, the method described in Visentin et al., 2016 (Talanta, 148, 478-485) cannot be used directly on complex media, such as, for example, sera/plasma from patients, and derivatives thereof. Indeed, the application of this method is confronted with technical problems associated with non-specific binding (NSB) of various constituents, more or less well known or unknown, from this type of sample, on the analysis surface. These problems of non-specific binding makes the interpretation of the results impossible.

Thus, despite the existing requirement to finely and precisely determine and characterize anti-HLA antibodies in complex biological samples, the SPR method cannot be applied to this type of sample. This requirement can be extended to other analyte-ligand pairs for which the same difficulties are encountered when complex samples are considered.

SUMMARY OF THE INVENTION

The subject of the invention makes it possible to solve the technical problems encountered during the application of the process for determining the active concentration of an analyte and optionally the kinetic constants of interaction of the analyte with a ligand in complex media such as human serum or plasma. Two years of development were necessary to obtain a suitable process.

The subject of the invention is therefore a particular embodiment of the SPR technique in capture mode, making it possible to obtain the parameters of active concentration and of kinetic interaction constants for complex samples, and thereby to meet existing clinical and research requirements.

The present invention relates to a method for determining, by surface plasmon resonance in complex biological samples, the active concentration of an analyte and optionally kinetic constants of interaction of the analyte with a ligand, comprising providing a surface plasmon resonance chip on which a capture agent specific to a ligand of the analyte is immobilized;

capture, by the capture agent, of a control ligand that does not bind the analyte to be tested;

passage of the sample over the chip, injected at a determined flow rate for a determined duration;

regeneration of the surface;

capture, by the capture agent, of a ligand that binds the analyte to be tested;

passage of the sample over the chip, injected at the same determined flow rate for the same determined duration;

subtraction of the sensorgram obtained with the control ligand from the sensorgram obtained with the ligand that binds the analyte to be tested; and calculation of the active concentration of the analyte, optionally determining the kinetic constants of interaction of the analyte with the ligand, and characterized in that the control ligand and the ligand that binds the analyte to be tested are of a similar mass and the control ligand and the ligand that binds the analyte to be tested are captured in equivalent amounts by the capture agent.

Preferably, the complex biological sample is selected from serum, plasma, urine, lavage liquids, ascites, biopsy eluates and cell culture media. In a preferred embodiment, the complex biological sample is serum or plasma.

In a first embodiment, the sample is injected at least two different flow rates and the active concentration of the analyte in the complex biological sample is calculated. Furthermore, the sample may be injected at different concentrations and the kinetic constants of interaction of the analyte with the ligand in the complex biological sample are calculated.

Preferably, the analyte-ligand pair is chosen from an antibody-antigen pair, a ligand-receptor pair, or a xenobiotic-molecular target pair.

In a particular embodiment, the analyte is an anti-HLA antibody, the control ligand is an HLA antigen not recognized by the antibody to be tested and the ligand that binds the analyte to be tested is a target HLA antigen of the antibody to be tested. The sample may undergo one or more prior treatments chosen from a heat treatment, a treatment with dithiothreitol (DTT), a step of purification of the IgGs on a protein G resin, a step of concentration of the sample, a step of dialysis, in particular with a cut-off threshold of 100 kDa, and a combination of several of these treatments. Preferably, the sample undergoes beforehand a combination of a heat treatment and a step of purification of the IgGs on a protein G resin. Preferably, the method comprises a prior step in which the anti-HLA antibodies in the sample are detected.

The present invention also relates to a kit suitable for the method according to the present invention, the kit comprising a surface plasmon resonance chip comprising at least two or three lanes chosen from the following lanes:

a lane on which a capture agent specific to HLA class I antigens, for example specific to β2 microglobulin, is immobilized;

a lane on which a capture agent specific to HLA-DQ antigens (class II) is immobilized;

a lane on which a capture agent specific to HLA-DR antigens (class II) is immobilized; and a lane on which a capture agent specific to HLA-DP antigens (class II) is immobilized.

DETAILED DESCRIPTION OF THE INVENTION

Since the method described in Visentin et al., 2016 (Talanta, 148, 478-485) cannot be used on complex media, such as, for example, sera/plasma from patients, and derivatives thereof, the inventors concentrated on developing this method for complex samples. Indeed, the application of this method is confronted with technical problems associated with non-specific binding (NSB) of various constituents, more or less well known or unknown, from this type of sample, on the analysis surface. Non-specific binding is intended to mean the undesired binding of molecules other than the analyte to the ligand. These problems of non-specific binding make it impossible to interpret the results. The aim of the invention was to discover technical solutions capable of correcting NSB. It then becomes possible to determine the active concentration of the analyte then the kinetic constants of interaction between the analyte and the ligand, and, by deduction, the affinity constant for their target of the analytes present in complex media such as biological liquids derived from human subjects. The invention can also be used with other media which may generate NSB, such as cell culture supernatants containing the antibodies to be studied. It should be noted that the determination of the kinetic interaction constants requires knowledge of the active concentration and that the active concentration per se is a parameter which may be of use, independently of the kinetic constants. The subject of the invention is the culmination of two years of experiments intended to make it possible to analyze complex media such as samples from patients and thus to eliminate the NSB that they systematically generate.

The inventors have discovered that each sample should be used as its own blank on a lane on which a HLA molecule, not recognized by the antibodies present in the sample, is captured in equivalent amounts to the target HLA molecule of these antibodies. This enables systematic correction of NSB and makes it possible to obtain reliable results. This test will be referred to as the auto-blank. This approach was tested by the inventors and proved effective on sera from patients.

This method, developed for the analysis of anti-HLA antibodies in complex samples, can be applied to the analysis of other analyte-ligand pairs in complex samples. This method can especially be applied to the analysis of analyte-ligand pairs chosen from an antibody-antigen pair, a ligand-receptor pair, or a xenobiotic-molecular target pair.

The present invention therefore relates to a method making it possible to determine the active concentration of an analyte and/or the kinetic constants of interaction between an analyte and a ligand in a complex sample, the method comprising:

providing a surface plasmon resonance chip on which a capture agent specific to a ligand of the analyte is immobilized;

capture, by the capture agent, of a control ligand that does not bind the analyte to be tested;

passage of the sample over the chip, injected at a determined flow rate for a defined time;

regeneration of the surface;

capture, by the capture agent, of a ligand that binds the analyte to be tested;

passage of the sample over the chip, injected at the same determined flow rate for the same defined time;

subtraction of the sensorgram obtained with the control ligand from the sensorgram obtained with the ligand that binds the analyte to be tested; and calculation of the active concentration of the analyte, optionally determining the kinetic constants of interaction of the analyte with the ligand, using the same surface after modification of the ligand capture and analyte injection parameters, and characterized in that the control ligand and the ligand that binds the analyte to be tested are of a similar mass and the control ligand and the ligand that binds the analyte to be tested are captured in equivalent amounts by the capture agent.

"Capture agent specific to a ligand of the analyte" denotes a molecule capable of establishing a specific bond with a ligand which is itself capable of interacting specifically with the analyte.

"Control ligand that does not bind the analyte to be tested" denotes a molecule capable of establishing a specific bond with the capture agent but incapable of establishing a specific bond with the analyte to be tested.

"Ligand that binds the analyte to be tested" denotes a molecule capable of establishing a specific bond with the capture agent and with the analyte to be tested. This ligand may also be denoted as target ligand in the present application.

Practical examples illustrating these designations are as follows.

In the context of an analyte-ligand pair which is an antibody-antigen pair, the capture agent is a molecule that has the ability to bind to the antigen, for example an antibody specific to the antigen, the control ligand is a molecule capable of being bound by the capture agent but not by the antibody, the ligand is the antigen, and the analyte is the antibody specific to the antigen. For example, the capture agent may also be an oligonucleotide aptamer. Aptamers are generally synthetic compounds, isolated in vitro from combinatorial libraries of a large number of randomly sequenced compounds by an iterative selection method referred to as SELEX.

In the context of an analyte-ligand pair which is a receptor-ligand pair, the capture agent is a molecule that has the ability to bind to the ligand, for example an antibody specific to the ligand, the control ligand is a molecule capable of being bound by the capture agent but not by the receptor, the ligand is the ligand of the receptor, and the analyte is the receptor specific to the ligand, or conversely the ligand may be the receptor and the analyte a ligand of the receptor.

In the context of an analyte-ligand pair which is a xenobiotic-molecular target pair, the capture agent is a molecule that has the ability to bind to the molecular target, for example an antibody specific to this target, the control ligand is a molecule capable of being bound by the capture agent but not by the xenobiotic, the ligand is the molecular target and the analyte is the xenobiotic.

Specific is intended to mean preferential fixation compared to others, preferably by a factor of at least 100, 1000 or 10 000.

"Sensorgram" is intended to mean the (graphical) representation of the SPR signal measured as a function of time, corresponding to the variation of the resonance angle due to the variation in mass in the field of the evanescent wave. The resonance signal is expressed in resonance units (RU).

Preferably, the sensorgrams are measured with a suitable Biacore machine, especially the Biacore T200, or equivalent.

When it is specified that the control ligand and the ligand that binds the analyte to be tested are of similar mass, this means that the ligands, when they become fixed to the capture agent, generate a substantially identical signal. Thus, in a particular embodiment, the masses thereof differ by no more than 10%, preferably by no more than 5%. Thus, for a ligand that binds the analyte to be tested of 100 kDa, the mass of the control ligand will be between 90-110 kDa, preferably between 95-105 kDa.

When "captured in equivalent amounts by the capture agent" is specified, this means that the amount of molecule captured, preferably measured in RU, is the same plus or minus 20%, preferably plus or minus 15%, even more preferably plus or minus 10%. The amount of molecule captured is preferably measured in RU.

It should be noted that the auto-blank step in the presence of the control ligand may be carried out before or after the step of testing the analyte with the target ligand.

In the specific context in which the analyte is an anti-HLA antibody, the present invention therefore relates to a method making it possible to determine the active concentration and/or the kinetic constants of interaction of anti-HLA antibodies to be tested with the HLA antigen recognized by the antibody in a complex sample, the method comprising:

providing a surface plasmon resonance chip on which a capture agent specific to the HLA antigens recognized by the antibody is immobilized;

capture or immobilization, by the capture agent, of an HLA antigen not recognized by the antibody to be tested;

passage of the sample over the chip, injected at a determined flow rate for a defined time;

regeneration of the surface;

capture, by the capture agent, of a target HLA antigen of the antibody to be tested;

passage of the sample over the chip, injected at the same determined flow rate for the same defined time;

subtraction of the sensorgram obtained with the HLA antigen not recognized by the anti-HLA antibody from the sensorgram obtained with the HLA antigen recognized by the anti-HLA antibody; and calculation of the active concentration of the antibody recognizing the HLA antigen, optionally determining the kinetic constants of interaction of the analyte with the ligand, using the same surface after modification of the ligand capture and analyte injection parameters, and characterized in that the HLA antigen not recognized by the antibody to be tested and the target HLA antigen of the antibody to be tested are captured in equivalent amounts by the capture agent.

It should be noted that the auto-blank step may be carried out before or after the step of testing the anti-HLA antibody with the target HLA antigen.

"Target HLA of the antibody" is intended to mean the HLA antigen recognized by the anti-HLA antibody.

The method relates most particularly to anti-HLA antibodies. Preferably, the antibodies are IgGs, especially IgG1s, IgG2s, IgG3s and/or IgG4s. More particularly, the method applies to IgGs in relation to IgMs.

Chip

The chip is a solid support suitable for SPR. Such chips are well known to those skilled in the art. The active surface consists of a matrix of polymers (dextran) fixed on a layer of gold via a linker (chemical link). The chip preferably comprises a layer of carboxymethylated dextran attached covalently to the thin layer of gold deposited on the surface. The matrix makes it possible to covalently immobilize the capture agent by virtue of simple chemical coupling using, for example, amine, thiol, hydroxyl, carboxyl or aldehyde groups. It is also possible to use a non-covalent system, i.e. capture system, for example by immobilizing an antibody that recognizes the capture agent (for example an anti-mouse IgG antibody if the capture agent is a mouse IgG) or else by immobilizing streptavidin or nickel conjugates in order to bind the capture agent which will have been functionalized beforehand with biotin or a histidine "tag", respectively.

Various compatible chips are commercially available (GE Healthcare, Xantec Bioanalytics). The chip is preferably a CM5 chip sold by GE Healthcare.

Capture Agent

The SPR chip has a capture agent immobilized on the surface thereof. This capture agent is capable of fixing a ligand specific to the analyte. The capture agent may bind directly to the ligand, for example be an antibody specific to the ligand. Alternatively, the capture agent may bind indirectly to the ligand, for example via a tag attached to the ligand and via an antibody directed against this tag. The tags may for example be polyhistidine tags, glutathione S-transferase tags, or equivalent.

The capture agent may be an antibody or an antibody derivative such as an antibody Fv, a single-domain antibody (dsFv or nanobody), a single chain antibody (scFv), a Fab, a F(ab')2, a Fab', an sc(Fv)2, or an oligonucleotide aptamer. This capture agent is immobilized on the chip by chemical coupling or a non-covalent bond of biotin-streptavidin type.

In the particular context of anti-HLA antibodies, the capture agent is specific to the HLA antigen for which the antibodies to be tested in the sample have an affinity.

When the antibody to be tested is an antibody directed against an HLA class I molecule, the capture agent is specific to this HLA class. It may for example be specific to β2 microglobulin (β2M) or to an HLA class I locus. Commercial antibodies specific to the HLA class I molecule, and preferably to human β2 microglobulin, are available, for example the clone B2M-01 (ThermoFisher Scientific, Rockford, Ill.), the clone B2M-02 (Abcam, France), the clone #883028 (R&D Systems, France) or the clone W6/32.

When the antibody to be tested is an antibody directed against an HLA class II molecule, the capture agent is specific to this class or to an HLA class II locus. It may for example be specifically directed against the antigens HLA-DR, HLA-DQ and/or HLA-DP. Specific commercial antibodies are available. There are especially antibodies having crossed specificities making it possible to recognize the majority of HLA class IIs such as the antibody of the Clone REA332 (Miltenyi Biotec) or the clone Tu39 (BD Biosciences, France). Alternatively, the method may employ pan-DQ antibodies such as the clone Tu169 (BD Biosciences, France) or the clone H1456 (One Lambda, Inc, Canoga Park, Calif.). Likewise, for the HLA-DR antigens, an anti-HLA-DR antibody will be used. Examples of such antibodies include the clone G46-6 (BD Bioscience), the clone H1458 (One Lambda) or the clone L243 (Biolegend). Finally, for the HLA-DP antigens, an anti-HLA-DP antibody will be used. Examples of such antibodies include the clone B7/21 (Abcam), the clone H143 (AbD Serotec), or the clone SP228 (Lifespan Bioscience).

Techniques for immobilizing capture agents on the surface of the chip are well known. Immobilization is preferably done via a covalent bond. For example, the coupling may be achieved via an amide bond in the presence of a mixture of N-hydroxysuccinimide and of N-ethyl-N'-dimethylaminopropyl carbodiimide, especially according to the supplier's instructions (GE Healthcare). This embodiment, in which the capture agent is immobilized covalently, has the advantage of obtaining a surface which can be regenerated. Alternatively, the capture agent may be immobilized via the streptavidin-biotin pair.

In one embodiment, the capture agent is immobilized on the surface in a sufficient amount. When the capture agent is an antibody, it may especially be immobilized so as to achieve at least 10 000 RU, preferably at least 15 000 RU, for example between 15 000 and 25 000 RU.

Samples

The samples under consideration in the present invention are complex biological samples. Blood samples such as serum and plasma, urine, liquids from lavages such as bronchoalveolar lavages, ascites, or else biopsy eluates and cell culture media are especially considered to be complex biological samples. In a preferred embodiment, the complex sample is a serum, in particular a human serum.

Before studying the sample by SPR, the sample may undergo prior treatments. The sample may especially undergo a heat treatment, a treatment with dithiothreitol (DTT), a step of purification of the IgGs on a protein G resin, a step of concentration of the sample, a step of dialysis, in particular with a cut-off threshold suitable for the analyte to be tested, and a combination of several of these treatments.

In a preferred embodiment, when the analyte is an antibody, in particular an anti-HLA antibody of IgG isotype, the sample is treated by a combination of a heat treatment and a step of purification of the IgGs. In an alternative preferred embodiment, the sample is treated by a combination of a heat treatment, a treatment with dithiothreitol (DTT), and a step of dialysis with a cut-off threshold of 100 kDa.

For example, the heat treatment may comprise a heat treatment consisting in incubation of the sample at 40-70° C., preferably 50-60° C., in particular 56° C., for 10-60 minutes, preferably 20-40 minutes, in particular 30 minutes.

The treatment with DTT may consist in adding DTT to the sample in order to reach a DTT concentration of 1-10 mM, preferably 5 mM, then heating to 30-40° C., preferably 37'C, for 10-60 minutes, preferably 20-40 minutes, in particular 30 minutes.

The IgGs may especially be purified on protein G-coupled Sepharose beads (ThermoFisher Scientific) or any other equivalent device, according to the supplier's recommendations. The purified compositions may be concentrated using Amicon Ultra-4 10 kDa centrifuges (ThermoFisher Scientific) or any other equivalent device, for example twice so as to return to a volume close to the initial volume.

The dialysis of the samples may be carried out against the running buffer using Float-A-Lyzer G2 dialysis devices with a 100 kDa cut-off (Spectrum Laboratories, Rancho Dominguez, Calif.) or any other equivalent device.

The samples may also be diluted or concentrated if necessary. They may especially be used in the method with several different levels of dilution.

The samples are preferably prepared in the running buffer. The running buffer is preferably a phosphate buffer that may comprise a detergent. In particular, the phosphate buffer may be at 0.01 M and contain TWEEN® 20 (0.05%). In a particular embodiment, the running buffer is PBS-T (Sigma-Aldrich) at 0.05%.

Capture by the Capture Agent of the Ligand

In order to produce the auto-blank, the surface must be loaded, via the capture agent, with a ligand which is not bound by the analyte to be tested. In order to carry out the measurement of the analyte to be tested, the surface must be loaded, via the capture agent, with the target ligand of the analyte. In a first embodiment, when the analyte is an anti-HLA antibody, the anti-HLA antibody recognizes an HLA class I. HLA class Is comprise a heavy chain, a β2 microglobulin (β2M) and a peptide. HLA class I comprise three large categories: HLA-As, HLA-Bs and HLA-Cs.

In a second embodiment, when the analyte is an anti-HLA antibody, the anti-HLA antibody recognizes an HLA class II. HLA class IIs comprise two chains α and β and a peptide. HLA class II comprise three large categories: HLA-DRs, HLA-DQs and HLA-DPs.

Thus, in order to produce the auto-blank, the surface must be loaded, via the capture agent, with an HLA antigen which is not recognized by the antibody to be tested. In order to carry out the measurement of the antibody to be tested, the surface must be loaded, via the capture agent, with the target HLA antigen, that is to say that which is recognized by the antibody to be tested.

Thus, the method preferably comprises a prior step in which the anti-HLA antibodies are detected in the sample. For example, the single antigen technique in Luminex® format (SAFB) may be employed, or any other equivalent method, for example an ELISA. Thus, at the end of this preliminary step, the nature of the anti-HLA antibodies contained in the sample is known and it is possible to determine which are the HLA antigens recognized by the anti-HLA antibodies present in the sample. Moreover, the method may also comprise a preliminary step of assaying total IgGs. For this purpose, we can implement for example an immunonephelometric assay on a BNII automated device (Siemens Healthcare Diagnostics, Marburg, Germany). The assay of total IgGs may preferably be carried out before and after treatment of the sample.

Preferably, the HLA antigen used to produce the auto-blank is in the same class as the antigen recognized by the antibody. This is because it is necessary for it to be recognized by the capture agent.

Thus, if the anti-HLA antibody to be tested is an antibody recognizing an HLA class I antigen, the antigen captured by the capture agent to produce the auto-blank will also be a class I antigen, which will for example be recognized by a capture agent specific to β2 microglobulin. For example, if the anti-HLA antibody to be tested is an antibody specific to HLA-A11, the antigen used for the auto-blank may be HLA-A2.

Alternatively, if the anti-HLA antibody to be tested is an antibody recognizing an HLA class II antigen, the antigen captured by the capture agent to produce the auto-blank will also be a class II antigen. For example, if the anti-HLA antibody to be tested is an antibody specific to HLA-DQ2, the antigen used for the auto-blank may be HLA-DQ7 or DQ5.

Determining the Active Concentration of the Analyte

Analysis by the CFCA method is well known to those skilled in the art and has especially been described in the papers by Karlsson et al (1993, J. Immunol. Methods, 166, 75-778) and Sigmundsson et al (2002, Biochemistry, 41, 8263-8276). The method for determining the active concentration by the CFCA method has especially been described in application WO2013/002717 (incorporated herein by reference). This method is used in the commercial system Biacore® (sold by GE Healthcare, Uppsala, Sweden).

Briefly, under the same conditions of concentration, temperature and solution, the SPR signal is measured as a function of time at two different flow rates of injection of the sample to be assayed. Analysis of the initial rate of association, which is different for each flow, makes it possible to determine the active concentration of the injected sample.

In order to produce the sensorgram, the sample is passed over the chip. More particularly, it is injected with a determined flow rate for a determined duration. It is especially necessary that the rate of diffusion of the analyte towards the surface is slower than the rate of association with the analyte with the target ligand. In the context of an analyte being an anti-HLA antibody, it is necessary that the rate of diffusion of the antibody towards the surface is slower than the rate of association with the target HLA antigen. In this context, a different initial association slope will be observed as a function of the flow rate and the comparison of the rates of association as a function of the flow rate used makes it possible to calculate the active concentration of the analyte. Thus, the sample is injected over the chip at two different flow rates, one slow flow rate and one fast flow rate, these two flow rates being chosen so as to obtain different initial association slopes. The conditions of temperature, concentration of the sample and injection time remain the same.

The chip is regenerated between two sensorgram measurements. Regeneration is intended to mean that the chip is brought back to its initial state, in which the surface bears only the capture agent. Regeneration solutions are well known to those skilled in the art, for example acid solutions, especially at a pH of less than 3.

The slow and fast flow rates are chosen such that the initial association slope at the slow flow rate is sufficiently large (greater than 0.3 RU/s at 5 μl/min) and that sensorgrams that are sufficiently different between the two flow rates are obtained. This difference is indicated by a "QC ratio" of greater than 0.2. The QC ratio is the Q quotient reflecting the degree of limitation of mass transport:

$$Q = \frac{\text{initial association slope at the fast flow rate}}{\text{initial association slope at the slow flow rate}} \times \sqrt[3]{\frac{\text{speed of the slow flow rate}}{\text{speed of the fast flow rate}}}$$

In particular, the fast flow rate is at least 5, 10, 15, 20 or 50 times faster than the slow flow rate. The fast flow rate may especially be 5, 10, 15, 20 or 50 times faster than the slow flow rate. For example, the slow flow rate may be from 2-20 μl/min, preferably from 2-10 l/min, and particularly preferably 5 l/min. The fast flow rate may be from 10-100 μl/min, preferably from 25-100 μl/min, and particularly preferably 100 l/min. The injection time may for example be from 30 to 100 s, preferably from 40 to 60 s, and preferably 50 s.

For determining the active concentration, capture of the greatest possible amount of ligand is desired.

Preferably, in the context of an analyte being an anti-HLA antibody, for determining the active concentration, the HLA antigen is captured by the capture agent in a large amount. Large amount is intended to mean that the amount of HLA antigen captured is at least 100 RU, preferably more than 200, 300 or 400 RU. In a preferred embodiment, the amount of HLA antigen immobilized is from 500 to 8000 RU. Preferably, the amount of HLA antigen immobilized is from 500 to 2000 RU.

The auto-blanks with the control ligands and the tests with the target ligands are carried out under the same conditions, except for the difference between the ligands.

The sensorgrams obtained with the auto-blanks are subtracted from the sensorgrams obtained with the target ligands. The active concentration of the analyte tested may thus be calculated.

Determining the Kinetic Constants of Interaction Between the Analyte and the Ligand SPR also makes it possible to determine the affinity of the anti-HLA antibody-HLA antigen complex by injecting increasing concentrations of analyte (and therefore of sample) over the surface. The experiments may be carried out in several cycles of association-dissociation then regeneration (multiple cycle kinetics analysis (MCK)) or by injecting increasing concentrations of the analyte until the target reaches saturation, without a regeneration cycle between the injections (single cycle kinetics analysis (SCK)).

Preferably, for determining the kinetic interaction constants, the ligand is captured by the capture agent in a small amount, in particular the smallest amount possible. In the context of an analyte which is an anti-HLA antibody, small amount is intended to mean that the amount of HLA antigen immobilized is at most 150 RU, preferably less than 100 RU. In a preferred embodiment, the amount of HLA antigen immobilized is from 20 to 100 RU, preferably from 50 to 100 RU.

In this context, the same temperature, the same flow rate and the same injection duration are used for variable concentrations of the analyte to be tested, and therefore different concentrations/dilutions of the biological sample. The sample is at least injected at two different concentrations, for example at 2, 3, 4, 5 or 6 concentrations. In a preferred embodiment, 3 different concentrations are used. Preferably, when the SCK method is used, the different concentrations are increasing. The different concentrations may vary by a factor of 2 to 10, for example by a factor of 2, 3, 4 or 5.

The injection speed or flow rate may for example be from 1-100 µl/min, preferably from 10-50 µl/min, and particularly preferably 25 µl/min.

The injection time may for example be from 10 to 100 s, preferably from 40 to 70 s, and preferably 60 s.

The auto-blanks and the tests with the target ligands are carried out under the same conditions, except for the difference of ligands.

The sensorgrams obtained with the auto-blanks are subtracted from the sensorgrams obtained with the target ligands.

The analysis software makes it possible to perform an adjustment or "fit" of the sensorgrams according to a given interaction model, most commonly a simple 1:1 bimolecular model. The elementary association and dissociation constants, $k_a$ and $k_d$ respectively, are determined directly from this analysis.

Kit

The present invention also relates to a kit suitable for carrying out the method according to the present invention.

In particular, the kit will comprise an SPR chip having several different lanes.

In one embodiment, in the context of an analyte/ligand pair, the chip may comprise one or more chosen lanes on which a capture agent specific to the ligand will be immobilized, as detailed above.

In a particular embodiment, in the context of an analyte which is an anti-HLA antibody, the chip may comprise one or more lanes chosen from the following lanes:
- a lane on which a capture agent specific to HLA class I antigens, for example specific to β2 microglobulin, will be immobilized;
- a lane on which a capture agent specific to HLA-DQ antigens (class II) will be immobilized;
- a lane on which a capture agent specific to HLA-DR antigens (class II) will be immobilized; and
- a lane on which a capture agent specific to HLA-DP antigens (class II) will be immobilized.

Preferably, the chip comprises at least two or three lanes chosen from the lanes mentioned above.

In a preferred embodiment, the chip comprises:
- a lane on which a capture agent specific to HLA class I antigens, for example specific to β2 microglobulin, will be immobilized;
- a lane on which a capture agent specific to HLA-DQ antigens (class II) will be immobilized; and
- a lane on which a capture agent specific to HLA-DR antigens (class II) will be immobilized.

In one embodiment, the SPR chip will also comprise a reference lane.

The kit may also comprise one or more HLA antigens, of use for producing auto-blanks and/or corresponding to the target HLAs of the anti-HLA antibodies for carrying out the tests.

The kit may also comprise one or more well-characterized anti-HLA antibodies which may serve as control.

The kit may also comprise reagents necessary for carrying out the present method, for example chosen from loading buffer, DTT, a protein G resin, etc. The kit may also comprise operating instructions.

The present invention also relates to the use of the kit as defined above for determining the active concentration of an analyte and/or the kinetic constants of association of the analyte with the ligand in a complex biological sample. In a particular embodiment, the present invention relates to the use of the kit as defined above for determining the active concentration and/or the kinetic constants of association of an anti-HLA antibody with the HLA antigen recognized by the antibody included in a complex biological sample.

Use of the Method

The invention is intended for clinical and research purposes.

The active concentration of the anti-HLA antibodies contained in complex media and their kinetic constants of interaction with their target are especially entirely unknown, while these parameters could be of vital importance in determining their pathological character, especially in the context of transplants. It should be noted that the determination of the kinetic interaction constants requires knowledge of the active concentration and that the active concentration per se is a parameter which may be of use, independently of the kinetic constants.

In a clinical context, determining these parameters could make it possible to determine the patients most at risk of losing their graft due to the presence of anti-HLA antibodies (diagnostic and prognostic interest), but also to monitor the effectiveness of a treatment (modifying the concentration of antibodies and/or of their affinity). After accumulating a large volume of clinical and biological data, it would perhaps be possible to improve strategies for matching donor/recipient pairs by choosing HLA antigens that are more "compatible" with one another, that is to say which induce the production of relatively weakly concentrated or low-affinity anti-HLA antibodies.

In research, it would be possible to use anti-HLA antibodies characterized in a precise manner, using the present invention, on in vitro models commonly employed in the field (endothelial cells, peripheral blood lymphocytes, etc.) and to study the impact of the active concentration and the kinetic constants on the mechanisms of pathogenicity of these antibodies: complement activation, cellular activation, antibody-dependent cell-mediated cytotoxicity. The invention would also make it possible to better understand the results given by the routine techniques of single antigen in Luminex® format and crossmatches by microlymphocytotoxicity and flow cytometry.

The method developed by the inventors has benefits in other fields of application and, non-exhaustively:

- for measuring the concentration of tumor markers in complex media such as human samples, for example beta-2-microglobulin (B2M), or prostate-specific antigen (PSA). In this context, the capture agent may for example be an anti-antibody antibody, the target ligand is an antibody specific to the tumor marker, and the control ligand is an antibody that does not have affinity for this marker.
- for assaying β2 microglobulin. Indeed, β2 microglobulin is a protein of 11 800 Da which is assayed on a daily basis in laboratories as a first-line marker in multiple myeloma and malignant B lymphopathies. The assaying thereof is also used in the prognosis and therapeutic monitoring of HIV infections, in monitoring chronic inflammatory diseases, in examining and monitoring renal function, in patients undergoing hemodialysis or those who have received a kidney transplant. The reference values thereof are of the order of 1 mg/ml (a bit more than 80 nM). In this context, the capture agent could be an anti-antibody antibody, the control ligand would be any antibody which does not have affinity for β2 microglobulin, and the target ligand would be an anti-β2 microglobulin antibody.
- for measuring the active concentration of antibodies directed against vaccine antigens and optionally defining their kinetic parameters of interaction with their target, in order to evaluate the effectiveness of a vaccine, for example. In this context, the capture agent could be an antibody directed against the antigen or a tag attached to the antigen, the control ligand would be a molecule different from the antigens but with a similar mass, and the target ligand would be one or more antigens of the vaccine. Likewise, a possible application relates to any antibody produced following an infection, in order to determine the effectiveness of an individual's response and their level of protection regarding the pathogen in question.
- for measuring the active concentration of cytokines and optionally defining their kinetic parameters of interaction with their receptor. In this context, the capture agent could be an antibody directed against the receptor or a tag attached to the receptor, the control ligand would be a receptor or a molecule that does not have affinity for the cytokine, and the target ligand would be the cytokine receptor. This would make it possible to determine the fraction of the cytokine capable of interacting with its receptor, it being knowing that some cytokines may be complexed with soluble receptors, which makes them inactive.
- for measuring the active concentration of pharmacological molecules and optionally defining their kinetic parameters of interaction with their target, for example by capturing their target using an anti-target or anti-tag antibody.
- for measuring the active concentration of anti-medicament antibodies and optionally defining their kinetic parameters of interaction with their medicament-based target. For example, immobilization of the target of a biotherapy (e.g.: TNFα), then capture of the biotherapy (anti-TNFα), and injection of the human sample over the surface. The auto-blank could be obtained using another biotherapy directed against TNFα.

EXAMPLES

Figure 1:
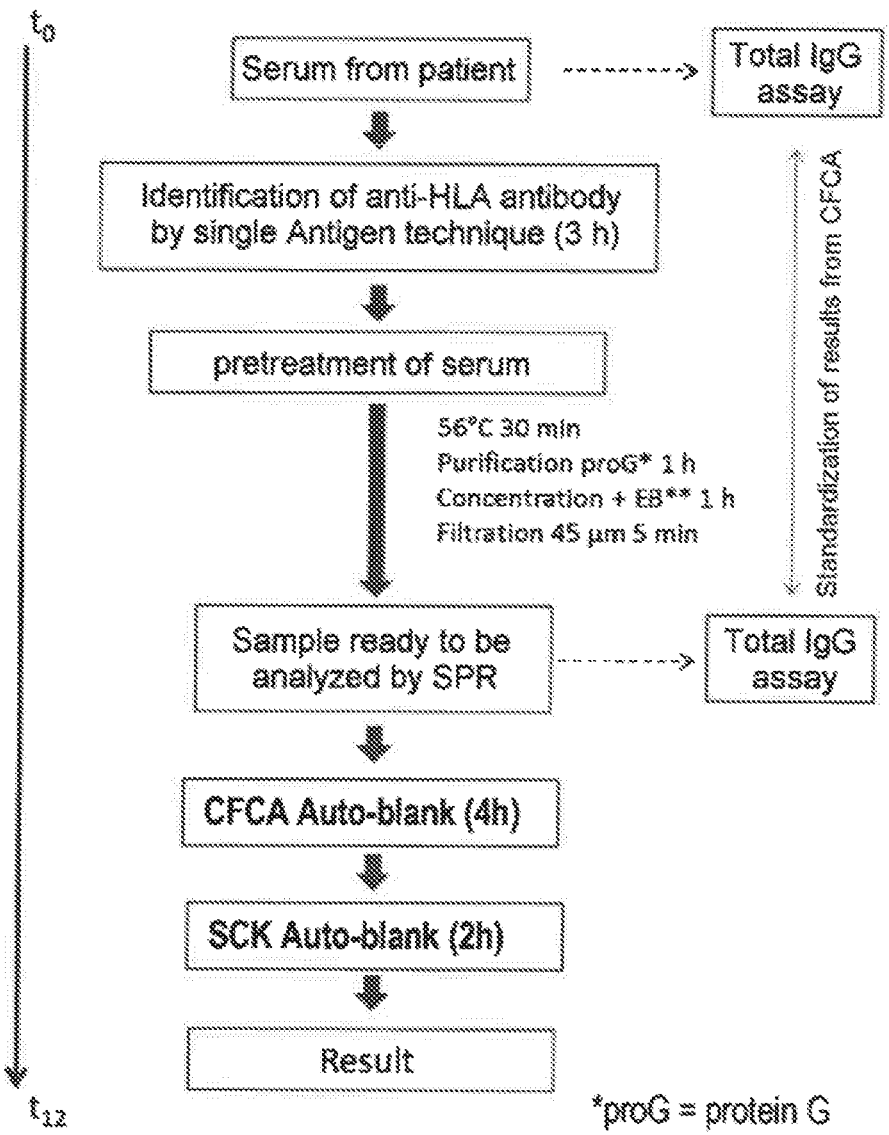
FIG. 1. Successive steps leading to the expected result from the patient's serum.

The subject of the invention is the culmination of two years of experiments intended to make it possible to analyze complex media such as samples from patients and thus to eliminate the NSB that they systematically exhibit.

The inventors first tested sera from patients diluted to 1/10 over the surface on which B2M-01 (mouse anti-B2M IgG2a) was immobilized (approximately 16 000 RU). All the sera showed strong interaction with the surface (table 1), whether or not the capture antibody was immobilized.

TABLE 1

Observation of NSB with sera from patients (1/10 dilution in PBS-T) on the reference lane (empty lane 3) and the lane with 16 000 RU of immobilized B2M-01. Values in RU. Flow rate 25 μl/min, injection duration = 1 min.

| Injection | Lane 3 (empty) | Lane 4 (B2M-01) | 4-3 |
|---|---|---|---|
| Serum 001 | 195 | 1871 | 1650 |
| Serum 003 | 59 | 2000 | 1900 |
| Serum 004 | 44 | 1544 | 1513 |
| Serum 005 | 61 | 1260 | 1195 |
| Serum 007 | 208 | 1988 | 1779 |
| Serum 010 | 87 | 1412 | 1300 |

Various treatments were applied to the samples in order to attempt to reduce NSB (elimination of small proteins by dialysis or complement inactivation). These treatments only proved to be partially effective since residual non-specific binding remained, to varying degrees. The residual NSB might not have posed a problem if it had been identical for all the patients. In this case, a serum or a mixture of sera devoid of anti-HLA could have been used as blank. However, it was observed that residual NSB was highly variable among the samples.

The inventors then undertook to purify the serum IgGs on protein G resins. The first results using purified IgGs diluted in PBS-T were not compelling. They even observed more NSB with the compositions purified on protein G, and that NSB was also variable on the reference lane as a function of the sample analyzed.

A certain number of other tests were carried out: denaturing the serum with heat, exhausting NSB by passing the sample over lanes upstream of the test lane with immobilized anti-B2M, pre-saturation of the lane with a pure serum, addition of BSA to the running buffer, deactivation of the surface, immobilization of the anchor on the reference lane. All also proved to be insufficiently effective.

At this stage of the investigations, the inventors accepted that it was impossible to reduce to zero the NSB obtained when samples originating from patients were used. Nonetheless, a crucial item of information obtained was that capturing HLA reduced NSB, most likely because the mass of proteins present on the chip was increased in comparison to the absence of capture.

Thus, the inventors had the idea of using each sample as its own blank on a lane on which an HLA molecule, not recognized by the antibodies present in the sample, is captured in equivalent amounts to the target HLA molecule of these antibodies.

The inventors first validated this method using monoclonal antibodies, used in derivatives of serum from non-anti-HLA-immunized patients, for which they determined the active concentration by CFCA. This was carried out for a mouse monoclonal anti-HLA class I antibody (anti-HLA-A2) (capture of the HLA molecules by an anti-B2M antibody, clone B2M-01) and a mouse monoclonal anti-HLA class II antibody (anti-DQ2) (capture of the HLA molecules by a commercial anti-DQ antibody, clone Tu169). The part of the process taking place on the SPR apparatus was as follows:

1—Immobilization of the capture antibody by chemical coupling on the SPR chip;
2—Carrying out the CFCA method:
  For the blank, firstly, an HLA antigen not recognized by the antibody to be tested is captured in a large amount on the surface, then the solution containing the antibody to be tested is injected at a determined flow rate for a determined duration. Finally, after a short period of dissociation, the surface is regenerated, which makes it possible to pass to a subsequent cycle.

For the test itself, firstly, the HLA antigen recognized by the antibody to be tested is captured in a large amount on the surface, then the solution containing the antibody to be tested is injected at the same determined flow rate for the same determined duration. Finally, after a short period of dissociation, the surface is regenerated, which makes it possible to pass to the following cycle.

The analysis software of the apparatus performs the correction by subtracting the sensorgram of the blank from the tests one; this is referred to as double-referencing.

The inventors were able to test the auto-blank under four different conditions for each class of HLA in comparison with the running buffer (RB; this is PBS-T). For this purpose, they used complex media derived from sera from patients with the following NSB characteristics (dilution ½ in PBS-T with 10% of "NSB reducer", a solution of dextran provided by GE Healthcare which is not however indispensable) (table 2):

TABLE 2

NSB of the samples used to validate the auto-blank method for CFCA. Flow rate 25 μl/min, injection duration = 1 min

| | Anchor | | | |
|---|---|---|---|---|
| | B2M-01 | | Tu169 (anti-DQ) | |
| Treatment of the serum | Heat + protein G | Heat + DTT + dialysis | Heat + protein G | Heat + DTT + dialysis |
| BOY | 20 | 341 | 24 | 29 |
| MOU | 28 | 235 | 49 | 75 |
| PIC | 23/17 | 151/120 | 24 | 32 |
| TAS | 30/25 | 423/349 | 22 | 45 |

This table highlights the heterogeneity of the NSB as a function of the samples and the pre-treatments but also of the anchor used. The following tests are applied to using different NSB samples, to which the method carried out in PBS-T was compared (table 3).

TABLE 3

CFCA of two monoclonal antibodies in complex media using the auto-blank method, in comparison with the method in simple medium "RB" which defines the concentration target. The auto-blank HLA molecule was HLA-A11 for anti-HLA-A2, and HLA-DQ7 for anti-HLA-DQ2. The QC ratio is an indicator of quality, which demonstrates the presence of mass transport. The results are 100% reliable if the QC ratio is greater than 0.2.

| | | Class I (A2OL-A2/A11) | | | DQ (DQ2OL-DQ2/DQ7) | | |
|---|---|---|---|---|---|---|---|
| | Sample | PIC | TAS | RB (target) | BOY | MOU | RB (target) |
| Heat + protein G | Concentration measured (nM) | 1.5 | 1.7 | 1.4 | 0.69 | 0.65 | 0.73 |
| | QC ratio | 0.549 | 0.509 | 0.558 | 0.446 | 0.464 | 0.399 |
| Heat + DTT + dialysis | Concentration measured (nM) | 0.96 | 1.8 | 1.4 | 0.96 | 0.91 | 1.3 |
| | QC ratio | 0.952 | 1 | 0.558 | 0.391 | 0.405 | 0.296 |

This table demonstrates the reliability of the results obtained by virtue of the auto-blank, the difference to the target being of the order of a tenth of a nM.

The inventors then tried this approach on 5 patients having anti-HLA DQ2 and DQ7 antibodies, the sera of which were treated with heat, DTT, and then dialyzed. The results are presented in table 4:

TABLE 4

CFCA of anti-HLA DQ antibodies from samples originating from sera from patients. These sera were identified as containing anti-HLA DQ2 or DQ7 antibodies by the Luminex ® Single Antigen (SAFB) technique, the fluorescence value (MFI) for which is specified in the table. The treatment applied to the sera was a heat treatment (56° C. 30 min), DTT (5 mM 37° C. 30 min) then dialysis against PBS-T (100 kDa membrane, 1 hour, 6 hours then overnight). The total IgG assay carried out before and after treatment of the serum makes it possible to determine the initial concentration of the IgG anti-HLAs present in the serum. For passage on the SPR apparatus, the samples were used diluted to ½ in PBS-T with 10% of "NSB reducer". For the anti-DQ2s (DQB1*02:01/DQA1*05:01), the auto-blank was carried out on captured HLA-DQ7, and vice versa for the anti-DQ7s.

|  | Target | SAFB MFI | Concentration (nM) | Corrected concentration (nM) | Initial IgG (g/l) | Final IgG (g/l) |
|---|---|---|---|---|---|---|
| BEL ½ | DQ2 | 11237 | 1.6 | 2.18 | 9.65 | 7.07 |
| BRI ½ | DQ2 | 20507 | 7.6 | 12.71 | 11.00 | 6.58 |
| LAP ½ | DQ2 | 15000 | 3.3 | 4.90 | 9.02 | 6.08 |
| PLA ½ | DQ7 | 20627 | 3.4 | 5.46 | 8.33 | 5.19 |
| THI ½ | DQ7 | 21464 | 2.1 | 2.83 | 11.60 | 8.61 |

It is interesting to note that the inventors did not observe a perfect relationship between the active concentration of the anti-HLA-DQs obtained by SPR and the MFI by SAFB. This suggests that the data obtained by SPR could provide different information. This could be crucial for patients.

It should be noted that there are large "buffer leaps" when using the serum treated with heat+DTT+dialysis, and that the time required to obtain a sample that is ready to be used on the Biacore platform is 24 hours (after identifying the antibodies by SAFB which lasts half a day). More recently, the inventors opted for the second pre-treatment mentioned, that is to say heat treatment of 1 ml of serum (56° C. for 30 min) then purification on protein G resin (1 hour), and finally concentration of the purified composition to return to an equivalent volume (1 to 1.2 ml) in PBS-T. Assaying the total IgGs before and after purification makes it possible to return to the initial concentration of the anti-HLA antibodies.

It is important to note that these two treatments make it possible to do away with anti-HLAs of IgM isotype that may be present in the serum of patients at the same time as the IgGs. These IgMs were identified as potentially interfering molecules in SAFB, but could also have interfered with the analysis of the anti-HLAs of IgG isotype by SPR.

FIG. 1 details the successive steps leading to the expected result from the patient's serum. The workflow presented in FIG. 1 shows that the time for carrying out the examination is entirely compatible with a clinical application, since the characterization of anti-HLA antibodies is not an urgent examination.

Figure 2:
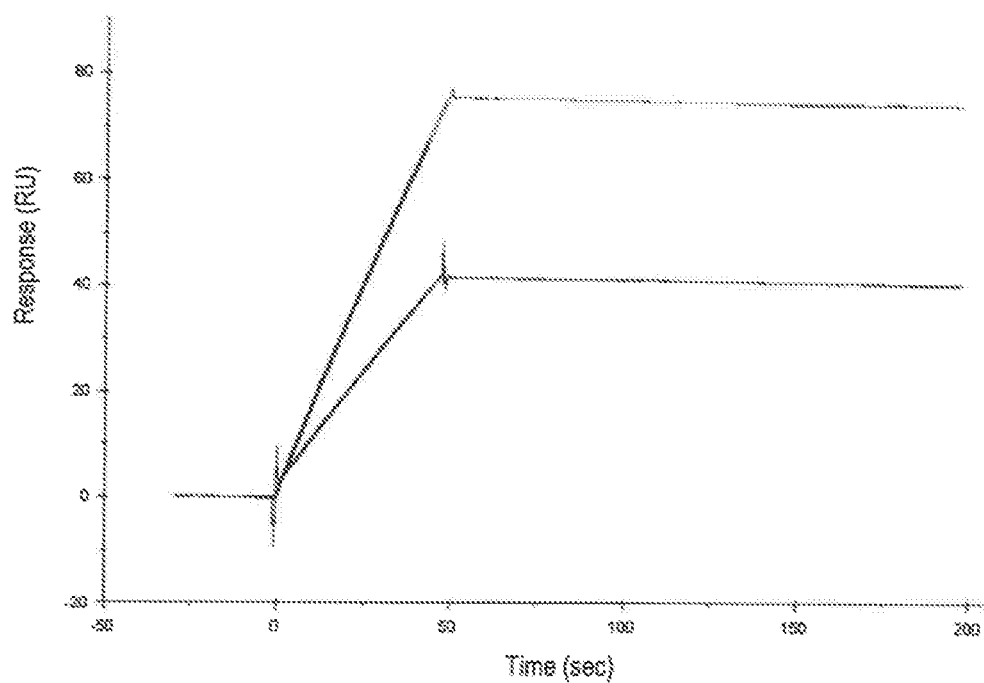
FIG. 2. CFCA auto-blank from a sample originating from the serum of a patient having anti-DQ2 antibodies (auto-blank DQ5). Dilution of the sample to 1/200, measured concentration 1.4 nM, concentration in the sample 270 nM, concentration in the serum after correction as a function of the IgG assays 460 nM, QC ratio 0.496.
Figure 3:
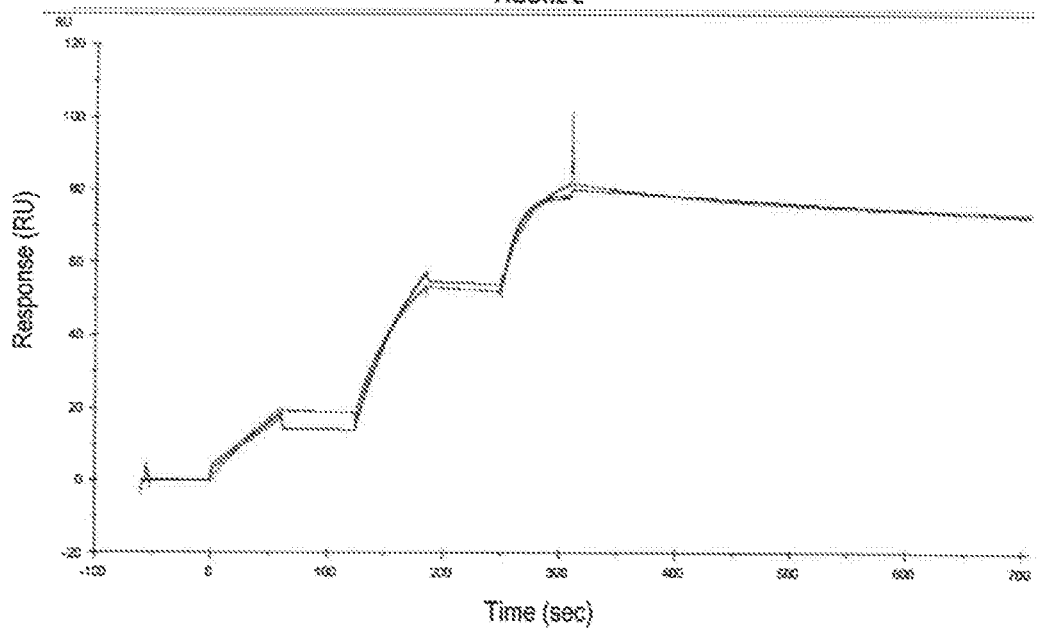
FIG. 3. SCK auto-blank from a sample originating from the serum of a patient having anti-DQ2 antibodies (auto-blank DQ5). Concentration used, deduced from the CFCA auto-blank: 2.16 nM, 10.8 nM and 54 nM. $k_a=1.493\times10^6$ $M^{-1}\cdot s^{-1}$, $k_d=2.482\times10^{-4}$ $s^{-1}$, $K_D=1.663\times10^{-10}$ M.

In the end, it is therefore entirely possible to obtain a result in two working days. The example of a patient having anti-DQ2 antibodies, studied by this process, is presented below. FIGS. 2 and 3 present the results from CFCA then SCK auto-blank. The fit of the sensorgrams to the kinetic interaction model is highly satisfactory, as shown by the superposition of the experimental curves and theoretical curves.

Figure 4:
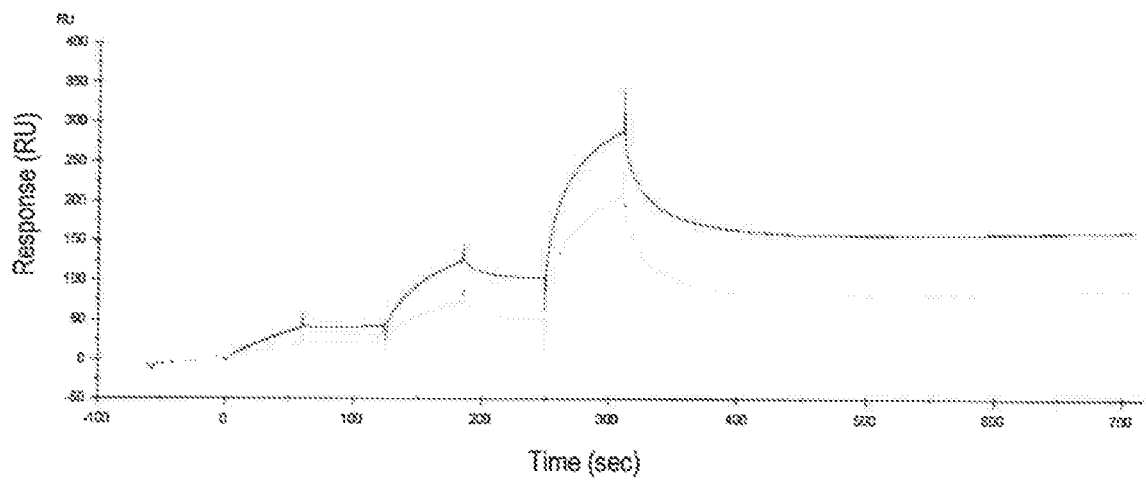
FIG. 4. Comparison of the blank (light sensorgrams) and of the reaction (dark sensorgrams) of an SCK auto-blank from a sample originating from the serum of a patient having anti-DQ2 antibodies (auto-blank DQ5).

FIG. 4 demonstrates the level of NSB during sample injection with increasing concentration, and the importance of using the auto-blank which makes it possible to correct this NSB. Indeed, strong binding to the lane clearly appears in the absence of the target HLA molecule.

The method is entirely reproducible (tables 5 and 6).

TABLE 5

CFCA auto-blank from a sample originating from the serum of a patient having anti-DQ2 antibodies (auto-blank DQ5). Dilution of the sample to 1/200 or 1/100 from frozen aliquots tested on different days.

|  | Dilution | Concentration measured (nM) | Concentration sample (nM) | QC ratio |
|---|---|---|---|---|
| Aliquot 1 | 200 | 1.4 | 270 | 0.496 |
| Aliquot 2 | 200 | 1.5 | 290 | 0.526 |
| Aliquot 3 | 100 | 3.2 | 320 | 0.439 |

TABLE 6

SCK auto-blank from a sample originating from the serum of a patient having anti-DQ2 antibodies (auto-blank DQ5). Tests carried out from frozen aliquots on different days.

|  | $k_a$ (1/Ms) | $k_d$ (1/s) | $K_D$ (M) |
|---|---|---|---|
| Aliquot 1 | $1.49 \times 10^6$ | $2.48 \times 10^{-4}$ | $1.66 \times 10^{-10}$ |
| Aliquot 2 | $1.36 \times 10^6$ | $2.37 \times 10^{-4}$ | $1.74 \times 10^{-10}$ |
| Aliquot 3 | $1.24 \times 10^6$ | $2.38 \times 10^{-4}$ | $1.90 \times 10^{-10}$ |

The inventors repeated the use of this approach on 10 additional patients having anti-HLA DQ2, DQ4, DQ6, DQ7, DQ9 antibodies and having received different types of transplant (lungs, heart, kidney, liver). The results are presented in table 7.

TABLE 7

CFCA and SCK of anti-HLA DQ antibodies from samples originating from sera from patients.
These sera were identified as containing anti-HLA DQ antibodies by the Luminex ®
Single Antigen (SAFB) technique, the fluorescence value (MFI) for which is specified in
the table (alpha chain associated with beta chain specified in brackets where relevant).

| Target HLA-DQ | Blank HLA-DQ | SAFB MFI | Concentration (nM) | Corrected concentration (nM) | Initial IgG (g/l) | Final IgG (g/l) | $k_a$ (1/Ms) | $k_d$ (1/s) | $K_D$ (M) |
|---|---|---|---|---|---|---|---|---|---|
| DQ2 (05) | DQ5 | 15570 | 5.2 | 7.85 | 10.4 | 6.90 | $5.71 \times 10^6$ | $5.59 \times 10^{-4}$ | $9.79 \times 10^{-11}$ |
| DQ2 (05) | DQ5 | 13802 | 15 | 24.15 | 11.3 | 7.02 | $2.43 \times 10^6$ | $1.37 \times 10^{-4}$ | $5.61 \times 10^{-11}$ |
| DQ7 | DQ5 | 20442 | 65 | 100.6 | 6.47 | 4.18 | $1.19 \times 10^6$ | $1.76 \times 10^{-4}$ | $1.50 \times 10^{-10}$ |
| DQ7 | DQ5 | 18172 | 14 | 22.3 | 13.2 | 8.3 | $2.13 \times 10^6$ | $1.80 \times 10^{-3}$ | $8.59 \times 10^{-10}$ |
| DQ7 | DQ5 | 20763 | 11 | 17.8 | 11.7 | 7.23 | $5.38 \times 10^6$ | $6.83 \times 10^{-4}$ | $1.27 \times 10^{-9}$ |
| DQ2 (05) | DQ5 | 23076 | 280 | 459.9 | 13.4 | 8.17 | $8.15 \times 10^6$ | $2.35 \times 10^{-4}$ | $2.88 \times 10^{-10}$ |
| DQ2 (02) | DQ6 | 18807 | 9.7 | 15.8 | 12.1 | 7.41 | $3.15 \times 10^6$ | $1.4 \times 10^{-3}$ | $4.58 \times 10^{-10}$ |
| DQ4 | DQ5 | 18401 | 27.0 | 40.0 | 7.49 | 5.06 | $1.72 \times 10^6$ | $4.29 \times 10^{-4}$ | $2.49 \times 10^{-10}$ |
| DQ6 | DQ5 | 21668 | 8.6 | 39.8 | 10.5 | 2.27 | $1.97 \times 10^6$ | $5.81 \times 10^{-4}$ | $2.95 \times 10^{-10}$ |
| DQ9 | DQ6 | 20000 | 14.0 | 21.3 | 4.29 | 2.82 | $1.52 \times 10^6$ | $5.93 \times 10^{-4}$ | $3.89 \times 10^{-10}$ |

The inventors also applied this approach to a system other than the anti-HLA antibodies, namely assaying beta-2 microglobulin (B2M) in complex media. The kinetic constants of interaction of B2M with its corresponding antibody were not measured since they do not have any clinical or biological significance.

Figure 5:
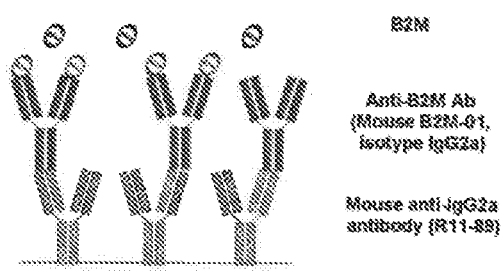
FIG. 5. System making it possible to measure the concentration of B2M by CFCA SPR in complex media.
Figure 5:
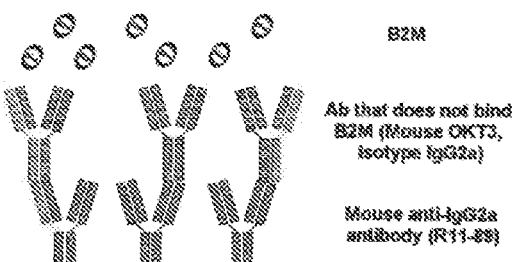

The part of the process taking place on the SPR apparatus was as follows (FIG. 5):

1—Immobilization of the capture antibody by chemical coupling on the SPR chip (mouse anti-IgG2a, clone R11-89, BD Biosciences);

2—Carrying out the CFCA method:

For the blank, firstly an antibody not recognizing B2M (clone OKT3, anti-CD3 antibody, BD Biosciences) was captured in a large amount on the surface, then the solution to be tested containing B2M was injected at a determined flow rate for a determined duration. Finally, after a short period of dissociation, the surface was regenerated, which made it possible to pass to a subsequent cycle.

For the test itself, firstly an antibody recognizing B2M (clone B2M-01) was captured in a large amount on the surface, then the solution containing B2M was injected at the same determined flow rate for the same determined duration. Finally, after a short period of dissociation, the surface was regenerated, which makes it possible to pass to the following cycle.

The analysis software of the apparatus performed the correction by subtracting the sensorgram of the blank from that of the test; this is referred to as double-referencing.

The concentration of a recombinant B2M solution (Thermo Fisher) diluted to 1/10 000 in running buffer (PBS-T) was firstly measured by capture CFCA, using running buffer as blank. The concentration measured was 4.3 nM.

Capture CFCA was then carried out in auto-blank in a complex medium (serum from a healthy subject, heat-treated, DTT-treated, then dialysed against PBS-T over 100 kDa membrane) used at 3 different dilutions and thereby giving rise to different levels of NSB. The NSB values recorded on the OKT3 antibody were as follows (table 8).

TABLE 8

Amount of NSB generated by the complex media used for validating the auto-blank in complex media for assaying B2M.

| Complex medium | NSB at flow rate of 5 µl/min (RU) | NSB at flow rate of 100 µl/min (RU) |
|---|---|---|
| Serum 1/10 | 342 | 575 |
| Serum 1/100 | 71 | 152 |
| Serum 1/1000 | 14 | 26 |

The concentrations of B2M measured in these samples were as follows (table 9).

TABLE 9

Assaying B2M by auto-blank capture CFCA within different complex media.

| Medium | Concentration measured (nM) |
|---|---|
| PBS-T | 4.3 |
| Serum 1/1000 | 4.0 |
| Serum 1/100 | 4.0 |
| Serum 1/10 | 4.7 |

Figure 6:
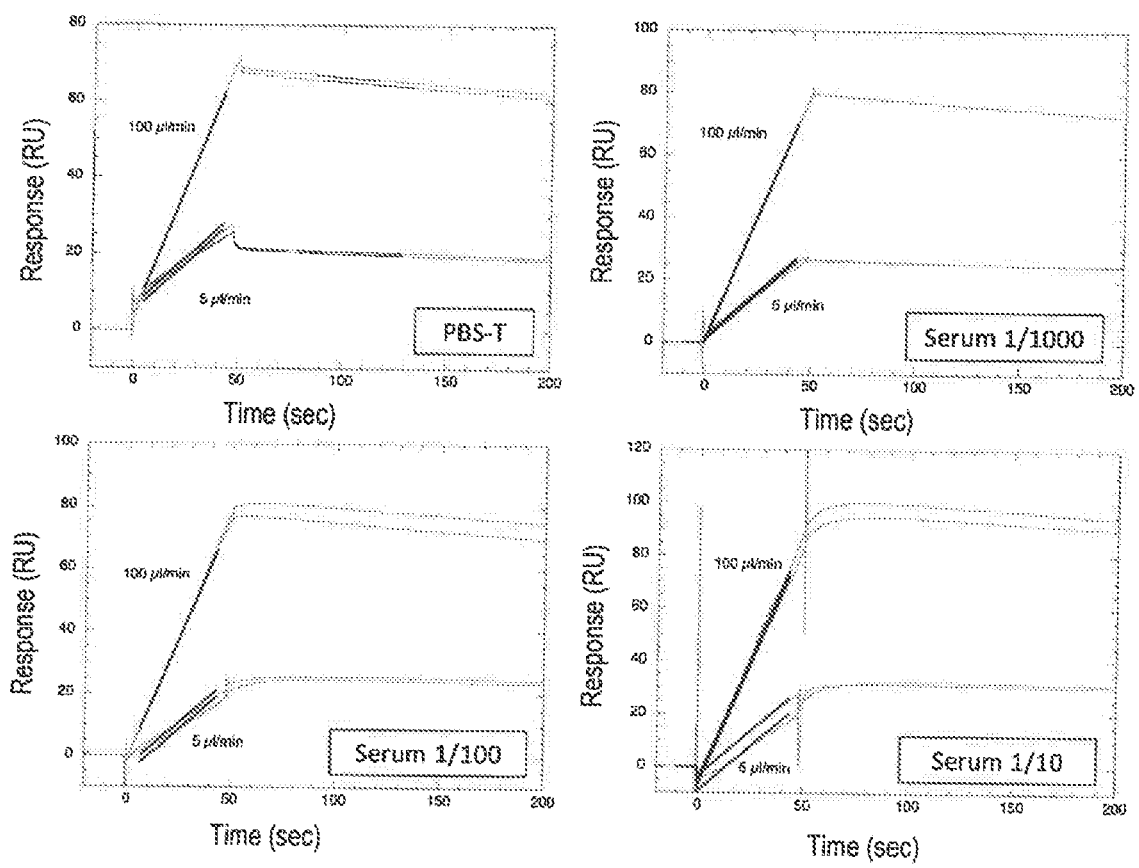
FIG. 6. CFCA sensorgrams for the B2M assay under different conditions: conventional blank (PBS-T) and auto-blank in a serum treated with DTT and dialyzed, diluted to 1/1000, 1/100 and 1/10. The sensorgrams are in gray, the adjustment made by the analysis software is in black.

The CFCA sensorgrams are presented in FIG. 6.

Materials and Methods

HLA Molecules and Antibodies

The monoclonal anti-HLA class I antibodies of murine origin used were: pan-class I W6/32 and anti-beta2-microglobulin (clone B2M-01) antibodies (ThermoFisher Scientific, Rockford, Ill.) and an anti-HLA-A2 antibody (One Lambda, Inc, Canoga Park, Calif.). The monoclonal anti-HLA class II antibodies of murine origin used were: pan-DQ antibody (clone Tu169) (BD Biosciences, Le Pont de Claix, France) and an anti-HLA-DQ2 antibody (One Lambda, Inc, Canoga Park, Calif.). The purified HLA molecules HLA-A*02:01 (A2), A*11:01 (A11), DQB1*02:01/DQA1*05:01 [DQ2(05)], DQB1*02:01/DQA1*02:01 [DQ2(02)], DQB1*03:01/DQA1*05:05 (DQ7), DQB1*03:03/DQA1*02:01 (DQ9), DQB1*04:01/DQA1*03:03 (DQ4), DQB1*05:01/DQA1*01:01 (DQ5) and DQB1*06:03/DQA1*01:03 (DQ6) were produced by One Lambda. An anti-CD3 antibody (clone OKT3, BD Biosciences) and mouse anti-IgG2a antibody (clone R11-89, BD Biosciences) were used.

Surface Plasmon Resonance (SPR) Experiments

The SPR experiments were carried out at 25° C. on a Biacore™ T200 (GE Healthcare Life Sciences, Uppsala, Sweden) with CM5 biochips (Biacore™). The sensorgrams were analyzed with the Biacore T200 Evaluation Software. The capture antibodies were immobilized with chemical coupling by amines, using a mixture of N-hydroxysuccinimide and N-ethyl-N'-dimethylaminopropyl carbodiimide according to the supplier's recommendations (GE Healthcare), after having been diluted in a solution of sodium acetate (10 mM, pH 5), followed by deactivation of the surface by injection of an ethanolamine solution (1 M, pH 8.5, GE Healthcare). A lane left without immobilization was used to perform a double correction of the sensorgrams. The peaks still present after this step were not removed since they do not affect the results. Unless indicated otherwise, the samples were prepared in PBS-T 0.05% which constituted the running buffer. The surface was regenerated by injection of a glycine solution (10 mM, pH 2.1, GE Healthcare) for 1 minute at 25 µl/min. For the tests for evaluation of non-specific binding (NSB), the samples were injected over the surface for 1 min at 25 µl/min, unless indicated otherwise.

Measurement of the Active Concentration

The calibration-free concentration analysis (CFCA) experiments were carried out after preliminary capture of the HLA ligands (900 s at 2 µl/min for class I, 840 s at 2 µl/min for class II) which were used in running buffer at a dilution enabling a high level of capture, in an equivalent amount for the same class. The anti-HLA antibodies were injected for 50 s at 5 µl/min then at 100 µl/min. All the samples and blanks were injected in duplicate. The coefficient of diffusion of the anti-HLA antibodies was calculated with the following formula:

$$D = 342.3 \times 1 / \left( \sqrt[3]{MW} \times f \times hrel \right) \times 10^{-11}$$

in which MW is the molecular weight (150 000 Da), f is the coefficient of friction (1.2 for globular proteins), and hrel is the relative viscosity (0.89 at 25° C.). The criteria for validating CFCA were those recommended by Biacore™, that is to say a sufficiently large initial association slope at a slow flow rate (greater than 0.3 RU/s at 5 µl/min) and sufficiently different sensorgrams between the two flow rates, as indicated by a "QC ratio" fit of greater than 0.2. The QC ratio is the Q quotient reflecting the degree of limitation of mass transport:

$$Q = \frac{\text{initial association slope at the fast flow rate}}{\text{initial association slope at the slow flow rate}} \times \sqrt[3]{\frac{\text{speed of the slow flow rate}}{\text{speed of the fast flow rate}}}$$

Measurement of the Kinetic Parameters

The kinetic parameters were determined on the same lanes as for the CFCAs, but by capturing a small amount of HLA (less than 100 RU) in order to avoid the kinetic artefacts sometimes observed with high ligand densities. The experiments were carried out at 25 µl/min using the single cycle kinetics (SCK) method: three increasing concentrations of the antibody were injected successively without regeneration between the injections. All the samples and blanks were injected in duplicate. The association and dissociation constants, $k_a$ and $k_d$, respectively, were determined by direct adjustment of the sensorgrams according to a Langmuir 1:1 interaction model. The dissociation equilibrium constant, $K_D$, was calculated to be equal to $k_d/k_a$.

Human Sera

The human sera used came from healthy subjects, from patients registered on the organ transplant wait list or patients who had received grafts. A milliliter thereof was used in different states, that is to say with or without pretreatment, with the possibility of having combined several pretreatments. The heat treatment consisted in incubation of the serum at 56° C. for 30 min. The treatment with dithiothreitol (DTT) consisted in the addition of DTT to the serum in order to reach a concentration of DTT of 5 mM then heating at 37° C. for 30 min. The serum IgGs were purified on Sepharose beads coupled to protein G (ThermoFisher Scientific), according to the supplier's recommendations. The purified compositions were concentrated using Amicon Ultra-4 10 kDa (ThermoFisher Scientific) centrifuges, twice over in order to return to a volume of 1150 µl in running buffer. The dialysis of the samples was carried out against the running buffer using Float-A-Lyzer G2 dialysis devices with a 100 kDa cut-off (Spectrum Laboratories, Rancho Dominguez, Calif.). All the samples were filtered over 0.45 µm filters before use. The total IgGs were assayed on sera treated and not treated by immunonephelometry on a BNII automated device (Siemens Healthcare Diagnostics, Marburg, Germany).

SAFB Tests

The sera were tested with the Luminex® Single Antigen kits after treatment in EDTA (10 mM final) according to the supplier's recommendations (One Lambda) and were analyzed on a Luminex 100® (Luminex, Austin, Tex.). The fluorescence intensities (MFI for mean fluorescence intensity) were standardized with the "baseline" formula (Fusion® software, One Lambda, Inc.).

Materials and Methods for Table 2

15 000 RU of antibodies were immobilized for the B2M-01 lane (class I), and 18 000 RU for the Tu169 lane (DQ). The human sera used originated from non-anti-HLA-immunized patients registered on the transplant wait list. These sera had undergone a heat treatment then purification of the IgGs on protein G and concentration in order to obtain 1 ml of purified composition, or else heat treatment followed by treatment with DTT and dialysis against running buffer. The samples treated were diluted to ½ in running buffer with 10% final of NSB reducer (GE Healthcare).

Materials and Methods for Table 3

15 000 RU of antibodies were immobilized for the B2M-01 lane (class I), and 18 000 RU for the Tu169 lane (DQ). The human sera used originated from non-anti-HLA-immunized patients registered on the transplant wait list. These sera had undergone a heat treatment then purification of the IgGs on protein G and concentration twice in order to obtain 1.15 ml of purified composition in running buffer, or else heat treatment followed by treatment with DTT and dialysis against running buffer. The A2OL (for anti-HLA-A2 One Lambda) and DQ2OL (for anti-DQ2 One Lambda) monoclonal antibodies were diluted to 1/2000 and 1/4000 in the treated sera diluted to ½ in running buffer with 10% final of background noise reducer, NSB reducer (GE Healthcare). For the A2OL, the blank was carried out by injecting this antibody over the surface on which a large amount of HLA-A11 was captured (1103+/−16 RU), and the test itself over a surface on which a large amount of HLA-A2 was captured (1014+/−18 RU). For the DQ2OL, the blank was carried out by injecting this antibody over the surface on which a large amount of HLA-DQ7 was captured (545+/−26 RU), and the test itself over a surface on which a large amount of HLA-DQ2 was captured (523+/−16 RU).

Materials and Methods for Table 4

Five sera from anti-HLA DQ2- or DQ7-immunized patients were heat-treated followed by a treatment with DTT and dialysis against running buffer. The IgGs were assayed in the serum before and after treatment. The Single Antigen test was carried out on serum treated with EDTA (SAFB MFI). The CFCA was carried out on these samples diluted to A in running buffer with 10% final of NSB reducer. For the patients with antibodies targeting HLA-DQ2, the blank was carried out by injecting the sample over the surface on which a large amount of HLA-DQ7 was captured, and the test itself over a surface on which a large amount of HLA-DQ2 was captured, and vice versa for patients with antibodies targeting HLA-DQ7. The levels of capture were 807+/−19 for HLA-DQ2 and 801+/−23 for HLA-DQ7, on a lane on which 20 000 RU of Tu169 were immobilized. The corrected concentration corresponds to the concentration initially present in the serum, obtained by deduction of the assays of total IgGs in the sera (initial IgG) and the treated samples (final IgG).

Materials and Methods for FIG. 2

A serum from an anti-HLA DQ2-immunized patient was heat-treated then underwent purification of the IgGs on protein G and concentration twice in order to obtain 1.15 ml of purified composition in running buffer. The CFCA was carried out on this sample diluted to 1/200 in running buffer with 10% final of NSB reducer. The blank was carried out by injecting the sample over the surface on which a large amount of HLA-DQ5 (818+/−2 RU) was captured. The test itself was carried out over a surface on which a large amount of HLA-DQ2 was captured (790+/−3 RU) by 15 000 RU of immobilized Tu169.

Materials and Methods for FIGS. 3 and 4

The SCK was carried out on the same sample as FIG. 2 at concentrations deduced from CFCA, injected in this order: 2.16 nM, 10.8 nM and 54 nM for 60 s at 25 μl/min, without regeneration between the injections. After the third injection, a 400 s period of dissociation was applied. The blank was carried out by injecting the sample over the surface on which a small amount of HLA-DQ5 (78+/−0 RU) was captured. The test itself was carried out over a surface on which a small amount of HLA-DQ2 was captured (82.5+/−0.7 RU) by 15 000 RU of immobilized Tu169.

Materials and Methods for Table 7

The treatment applied to the sera was exposure to heat then purification of the IgGs on protein G and concentration twice in order to obtain 1.15 ml of purified composition in running buffer. The CFCA was carried out on these samples diluted from Y to 1/200 in running buffer with 10% final of NSB reducer. The blank was carried out by injecting the sample over the surface on which a large amount of HLA-DQ not recognized by the patient's serum was captured by 10 300 RU of immobilized Tu169. The test itself was carried out over the same surface on which an amount of target HLA-DQ was captured in an equivalent amount to the antigen used for the blank. The SCKs were carried out on the same samples and analysis lanes at increasing concentrations deduced from the CFCA, for 60 s at 25 μl/min, without regeneration between the injections. After the third injection, a 400 s period of dissociation was applied. The blank was carried out by injecting the sample over the surface on which a small amount of HLA-DQ not recognized by the patient's serum was captured. The test itself was carried out over the same surface on which an amount of target HLA-DQ was captured in an equivalent amount to the antigen used for the blank.

Materials and methods for FIG. 6

A mouse clone anti-IgG2a antibody (R11-89, BD Biosciences) was immobilized at a level of 13 000 RU by chemical coupling on a CM5 chip. The concentration of a beta-2 microglobulin (B2M) solution diluted to 1/10 000 in running buffer (PBS-T) was firstly measured by capture CFCA, capturing 2400 RU of an antibody recognizing B2M (clone B2M-01) and using running buffer (PBS-T) as blank. The measurement of the B2M concentration was then repeated using the auto-blank method and by diluting it in 3 different complex media giving different levels of non-specific binding ("serum 1/1000", "serum 1/100" and "serum 1/10"). The auto-blank condition consisted in the capture, at an equivalent level to the B2M-01 antibody, of an antibody of IgG2a isotype that does not bind B2M (clone OKT3, anti-CD3 antibody, BD Biosciences).

The invention claimed is:

1. A method for determining, by surface plasmon resonance in complex biological samples, active concentrations of an analyte and optionally kinetic constants of interaction of the analyte with a ligand, comprising
    providing a surface plasmon resonance chip on which a capture agent specific to a ligand of the analyte is immobilized;
    capture, by the capture agent, of a control ligand that does not bind the analyte to be tested;
    passage of the sample over the chip, injected at a determined flow rate for a determined duration and obtaining a sensorgram for the control ligand;
    regeneration of the surface to remove the captured control ligand from the capture agent;
    capture, by the capture agent, of a ligand that binds the analyte to be tested;
    passage of the sample over the chip, injected at the same determined flow rate for the same determined duration and obtaining a sensorgram for the analyte;
    subtraction of the sensorgram obtained with the control ligand from the sensorgram obtained with the ligand that binds the analyte to be tested; and
    calculation of the active concentration of the analyte and optionally kinetic constants of interaction of the analyte with the ligand,
    and characterized in that the control ligand and the ligand that binds the analyte to be tested are of a similar mass and the control ligand and the ligand that binds the analyte to be tested are captured in equivalent amounts by the capture agent.

2. The method as claimed in claim 1, characterized in that the complex biological sample is selected from serum, plasma, urine, lavage liquids, ascites, biopsy eluates and cell culture media.

3. The method as claimed in claim 2, characterized in that the complex biological sample is serum or plasma.

4. The method as claimed in claim 1, characterized in that the sample is injected at least two different flow rates and that the active concentration of the analyte in the complex biological sample is calculated.

5. The method as claimed in claim 1, characterized in that the sample is injected at different concentrations and that the kinetic constants of interaction of the analyte with the ligand in the complex biological sample are calculated.

6. The method as claimed in claim 1, characterized in that the analyte-ligand pair is chosen from an antibody-antigen pair, a ligand-receptor pair or a xenobiotic-molecular target pair.

7. The method as claimed in claim 1, characterized in that the analyte is an anti-HLA antibody, the control ligand is an HLA antigen not recognized by the antibody to be tested and the ligand that binds the analyte to be tested is a target HLA antigen of the antibody to be tested.

8. The method as claimed in claim 7, characterized in that the sample undergoes one or more prior treatments chosen from a heat treatment, a treatment with dithiothreitol (DTT), a step of purification of the IgGs on a protein G resin, a step of concentration of the sample, a step of dialysis, in particular with a cut-off threshold of 100 kDa, and a combination of several of these treatments.

9. The method as claimed in claim 8, characterized in that the sample previously undergoes a combination of a heat treatment and a step of purification of the IgGs on a protein G resin.

10. The method as claimed in claim 9, characterized in that the method comprises a prior step in which the anti-HLA antibodies in the sample are detected.

11. The method as claimed in claim 8, characterized in that the method comprises a prior step in which the anti-HLA antibodies in the sample are detected.

* * * * *

UNITED STATES PATENT AND TRADEMARK OFFICE
CERTIFICATE OF CORRECTION

PATENT NO. : 11,079,375 B2
APPLICATION NO. : 16/083529
DATED : August 3, 2021
INVENTOR(S) : Jonathan Visentin, Carmelo Di Primo and Jean-Luc Taupin Page 1 of 1

It is certified that error appears in the above-identified patent and that said Letters Patent is hereby corrected as shown below:

In the Specification

Column 12,
Line 48, "2-10 l/min," should read --2-10 µl/min,--.
Line 49, "5 l/min." should read --5 µl/min.--.
Line 51, "100 l/min." should read --100 µl/min.--.

Column 25,
Line 11, "to A in" should read --to ½ in--.

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*